(12) United States Patent
Zahler et al.

(10) Patent No.: US 8,500,173 B2
(45) Date of Patent: Aug. 6, 2013

(54) MEDICAL-ENGINEERING COUPLING MECHANISM FOR CONNECTING TWO MEDICAL INSTRUMENTS

(75) Inventors: Sabine Zahler, Vaterstetten (DE);
Sebastian Frey, Waghaeusel (DE);
Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 874 days.

(21) Appl. No.: 11/683,189

(22) Filed: Mar. 7, 2007

(65) Prior Publication Data

US 2007/0213691 A1    Sep. 13, 2007

(30) Foreign Application Priority Data

Mar. 7, 2006 (DE) .......................... 10 2006 010 316

(51) Int. Cl.
*F16L 37/086* (2006.01)

(52) U.S. Cl.
USPC ............................ 285/317; 285/308; 285/901

(58) Field of Classification Search
USPC ............. 285/33, 34, 308, 317, 319, 322, 323, 285/901; 138/89; 403/109.2, 109.3, 109.8, 403/322.1, 322.2, 328
See application file for complete search history.

(56) References Cited

U.S. PATENT DOCUMENTS

| | | | |
|---|---|---|---|
| 3,735,928 A * | 5/1973 | Watts et al. ................... | 239/267 |
| 4,856,823 A | 8/1989 | Heren | |
| 5,374,088 A | 12/1994 | Moretti et al. ................. | 285/305 |
| 5,378,025 A * | 1/1995 | Szabo ............................... | 285/39 |
| 5,607,190 A * | 3/1997 | Exandier et al. ................. | 285/93 |
| 5,653,475 A | 8/1997 | Scheyhing et al. | |
| 6,672,628 B2 | 1/2004 | Thomas et al. ................. | 285/320 |
| 6,767,155 B2 * | 7/2004 | O'Brien et al. ............. | 403/322.1 |
| 7,316,425 B2 * | 1/2008 | Poder .............................. | 285/93 |
| 7,431,346 B2 * | 10/2008 | Frost et al. ..................... | 285/317 |
| 7,490,865 B1 * | 2/2009 | Tsai ................................ | 285/322 |
| 2003/0122372 A1 * | 7/2003 | Muto ................................ | 285/39 |
| 2003/0155765 A1 | 8/2003 | Thomas et al. | |

(Continued)

FOREIGN PATENT DOCUMENTS

| | | |
|---|---|---|
| AT | 397 137 B | 2/1994 |
| DE | 4035581 A1 | 5/1991 |

(Continued)

OTHER PUBLICATIONS

German Search Report, Feb. 13, 2007, (4 pages).

(Continued)

*Primary Examiner* — James Hewitt
(74) *Attorney, Agent, or Firm* — St. Onge Steward Johnston & Reens LLC

(57) ABSTRACT

A medical-engineering coupling mechanism for connecting two medical instruments having a coupling plug and a coupling socket for inserting the coupling plug, so that the coupling socket and the coupling plug can be secured to one another by at least one spring-loaded notching connection. To produce a medical-engineering coupling mechanism that is easy to manipulate and ensures a secure notching connection of the components that are to be connected to one another, it is proposed with the invention that the notching connection consists of at least two notching hooks that are positioned on one of the components and are in active engagement with at least one spring element configured as a spring washer, and at least one notching recess positioned on the other component for insertion of the at least two notching hooks.

14 Claims, 6 Drawing Sheets

U.S. PATENT DOCUMENTS

| | | | |
|---|---|---|---|
| 2004/0150223 A1* | 8/2004 | Campau | 285/308 |
| 2005/0121910 A1* | 6/2005 | Muto | 285/322 |
| 2005/0179258 A1* | 8/2005 | Brandt et al. | 285/308 |
| 2005/0206160 A1* | 9/2005 | Ericksen et al. | 285/308 |
| 2005/0225082 A1 | 10/2005 | Dalle et al. | |
| 2006/0058579 A1* | 3/2006 | Oberlaender et al. | 600/102 |
| 2007/0029796 A1* | 2/2007 | Bibby | 285/308 |
| 2008/0129047 A1* | 6/2008 | Blivet et al. | 285/308 |
| 2008/0199252 A1* | 8/2008 | Frey et al. | 403/325 |
| 2009/0200796 A1* | 8/2009 | Lai | 285/317 |

FOREIGN PATENT DOCUMENTS

| | | |
|---|---|---|
| DE | 4300037 C1 | 4/1994 |
| DE | 44 25 705 A1 | 1/1996 |
| DE | 297 10 025 U1 | 8/1997 |
| DE | 198 44 583 A1 | 4/2000 |
| EP | 0990831 A1 | 4/2000 |

OTHER PUBLICATIONS

European Search Report, EP07003182, Nov. 19, 2007, 9 pages.

\* cited by examiner

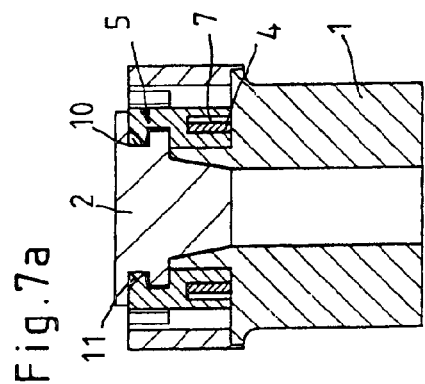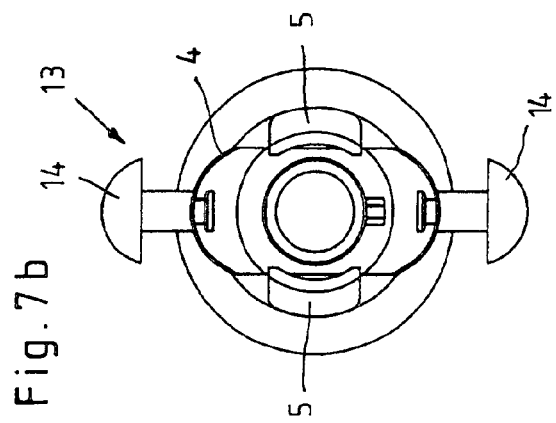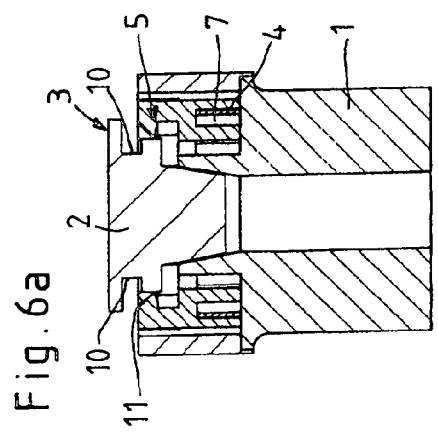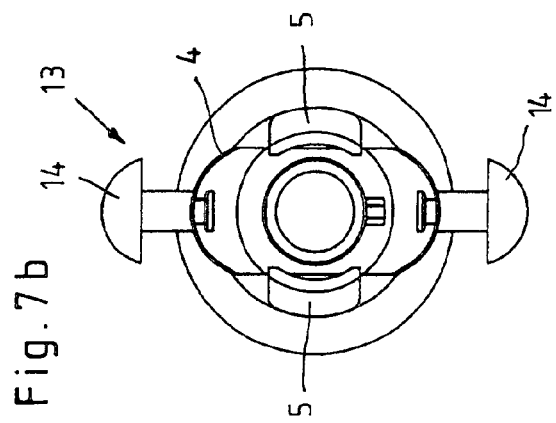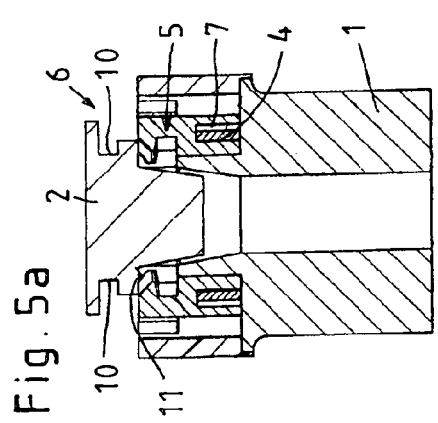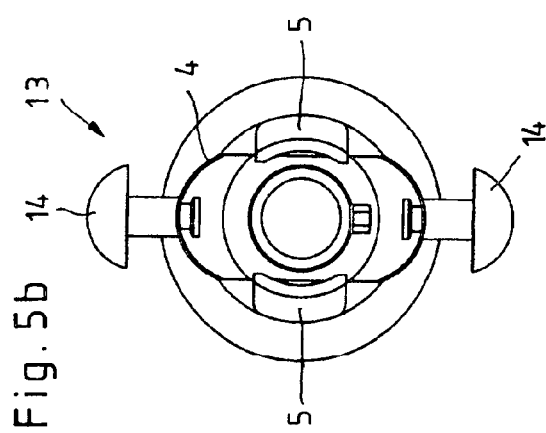

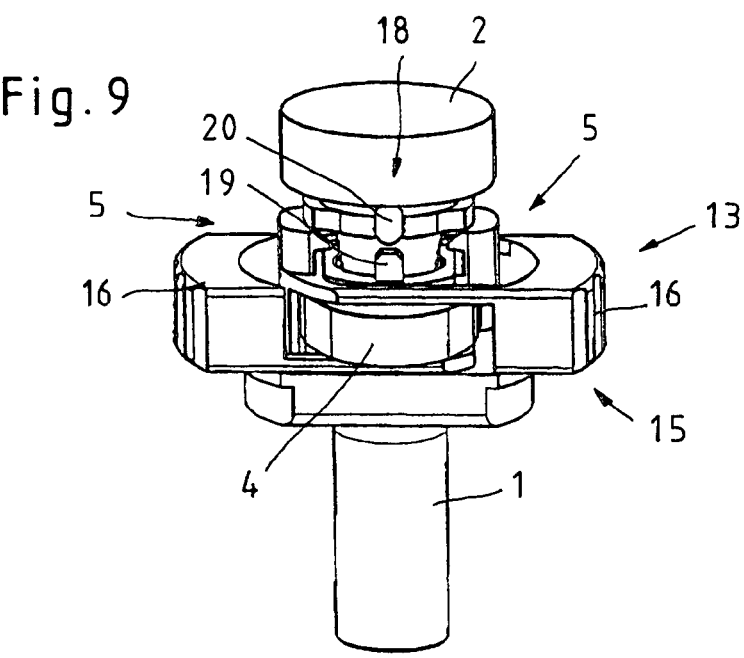
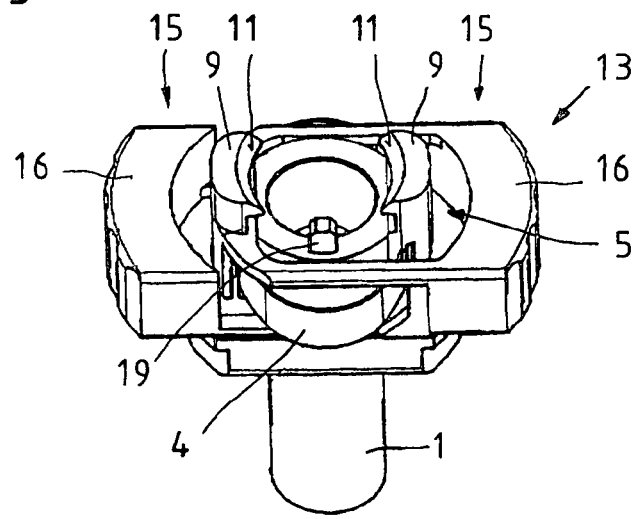

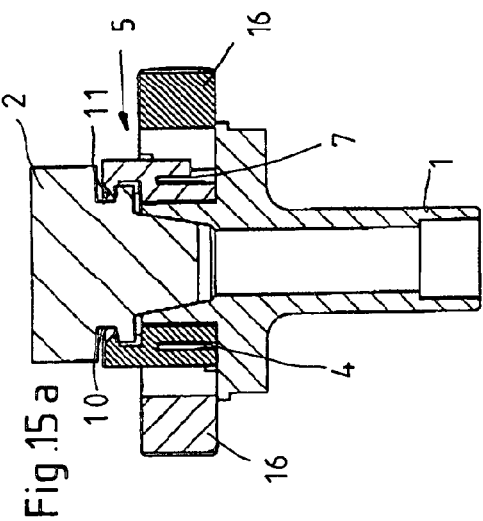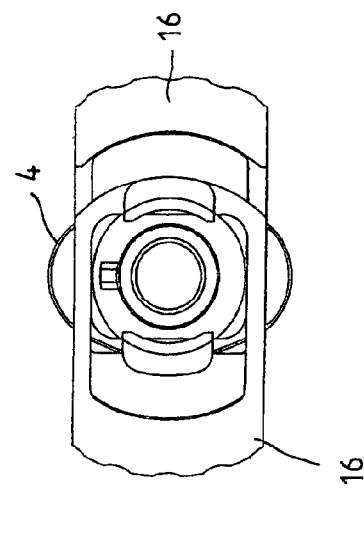
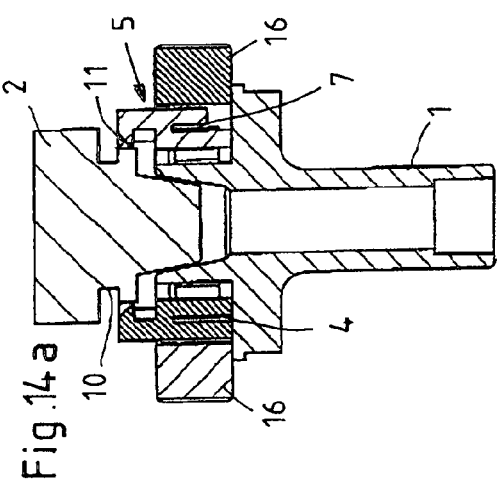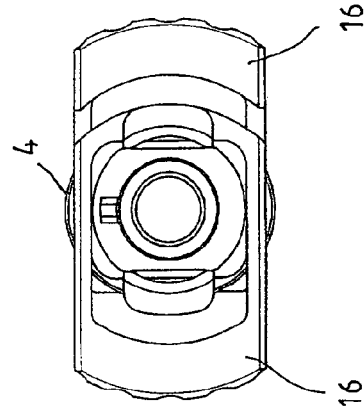
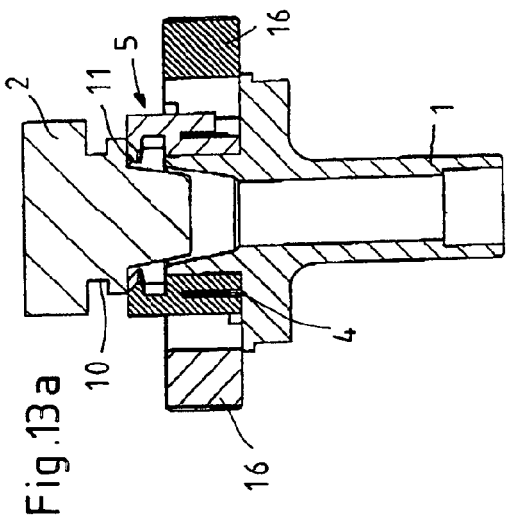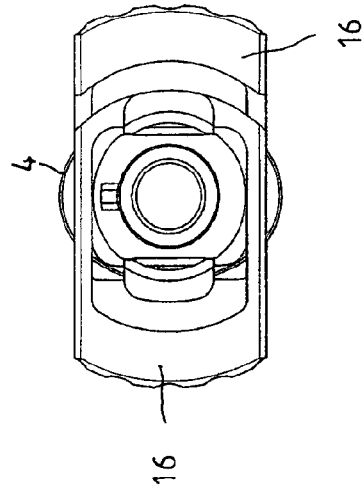

MEDICAL-ENGINEERING COUPLING MECHANISM FOR CONNECTING TWO MEDICAL INSTRUMENTS

CROSS-REFERENCE TO RELATED APPLICATIONS

The present application claims priority of German patent application No. 10 2006 010 316.5 filed on Mar. 7, 2006, the content of which is incorporated herein by reference.

FIELD OF THE INVENTION

The invention relates to a medical-engineering coupling mechanism for connecting two medical instruments, in particular instruments for endoscopic surgery, having a coupling plug and a coupling socket for insertion of the coupling plug, so that the coupling socket and the coupling plug can be secured to one another by means of a spring-loaded click-stop connection.

BACKGROUND OF THE INVENTION

A generic medical-engineering coupling mechanism is familiar in the prior art, for instance from DE 44 25 705 C2. This known coupling mechanism is a component in an endoscopic instrument, so that the coupling socket is configured at the proximal end of the instrument and the coupling plug is a component of a second instrument that is to be connected with this endoscopic instrument. This known coupling mechanism consists of a bayonet coupling as well as a spring-loaded notching element by which the two components can be fixed against one another. This known coupling mechanism has proved itself extensively in practice; however, the structure with a bayonet coupling and a click-stop element is complex. In addition it requires a separate manual rotation of a rotary ring in order to fix the two components to one another.

Consequently it is the object of the invention to create a medical-engineering coupling mechanism of the aforementioned type, which ensures simple handling as well as a secure notching connection of the components that are to be joined with one another.

SUMMARY OF THE INVENTION

This object is fulfilled according to the invention in such a way that the notching connection consists of at least two notching hooks positioned on one of the components to be connected to one another, and in active engagement with at least one spring element configured as a spring washer, as well as at least one notching recess positioned on the other component for insertion of the at least two notching hooks.

Because of the inventive configuration of the medical-engineering coupling mechanism, it is possible, merely by pushing them together, to make a watertight connection of the two components that are to be joined. With the inventive mechanism there is no need for an additional manual action or the use of an implement.

According to an advantageous embodiment of the invention, it is proposed that the spring washer should have an elliptical shape when viewed from above. The elliptical shape permits an especially good malleability of the washer ring by applying lateral pressure.

To produce a washer ring that is highly resistant to breakage while ensuring high spring power, the inventive spring washer consists advantageously of metal, preferably spring steel.

The active engagement between the notching hooks and the at least one spring washer, according to a practical embodiment of the invention, is produced in that a groove for insertion of the spring element is configured in the notching hooks. The notching hooks thus are almost sitting upright on the spring washer, so that a direct reciprocal effect is produced between the spring force of the spring washer and the mobility of the notching hooks.

It is further proposed with the invention that in the area above the groove at least one stud extending outward is configured on each of the notching hooks and this stud is in contact with the spring element when the spring element is positioned in the groove. Because of this stud in contact with the spring element, the spring washer is always pressed downward to secure its position, so that it is not possible for the spring washer to slip upward when the spring washer is pressed together.

According to a preferred embodiment of the inventive coupling mechanism, it is proposed that the notching hooks are positioned on the coupling socket and the notching recess is positioned on the coupling plug. It is also possible, of course, to configure the coupling mechanism in such a way that the notching hooks are configured on the coupling plug and the notching recess on the coupling socket.

For configuring the inventive notching hooks, on the notching hooks there are notches pointing inward, which when notched together engage in the notching recess that is configured as a surrounding groove.

It is possible to facilitate the notching with the notching hooks according to the invention in that starter slopes pointing inward are positioned on the upper side of the notches, so that the notching hooks are automatically pressed outward when running up against the component that is to be notched together.

In order, first, to create an especially axial tolerance compensation in the configuration of the notching hooks and notching recesses and, second, to ensure a constantly secure notching along with simultaneous water-tight insulation, it is proposed with the invention that on the underside of the notches there are bevels configured. These bevels, which advantageously span an angle of 5 to 15 degrees, preferably 10 degrees, with the horizontal plane, work together with the spring force of the spring washer to cause the notching, in self-inhibiting manner, to be always pressed together in the direction of the notching position.

To separate the components connected with one another by means of the inventive coupling mechanism, the notching connection can be released again by a release mechanism that stands in active engagement with at least one spring element.

According to a first embodiment of the invention it is proposed that the release mechanism includes at least two actuation buttons positioned on the spring element, by which buttons the spring element can be pressed together so that the actuation buttons are advantageously positioned so that they are offset from the notching hooks on the spring element.

According to an alternative second embodiment of the invention, the release mechanism includes at least two sliding members, such that each sliding member is configured as a single unit with one notching hook in such a way that an actuation part of the sliding member is positioned on the sliding member at an 180 degree angle to the respective notching hook.

Finally it is proposed with the invention that guide and/or positioning elements are configured, corresponding to one another, on the coupling plug and on the coupling socket in order to ensure precisely located and rotation-proof placement of the components with respect to one another.

The invention also relates to a coupling socket for insertion of a coupling plug of a medical-engineering coupling mechanism, in particular instruments for endoscopic surgery, so that the coupling socket and the coupling plug can be secured to one another by at least one spring-loaded notching connection. Because the coupling plug in practical embodiments of this type of medical coupling mechanisms is frequently configured on a multiple-use standard instrument, for instance an endoscope lens, which can be coupled with various other medical instruments by means of a coupling socket, the inventive coupling socket is characterized in that the notching connection consists of at least two notching hooks positioned on the components that are to be connected to one another and in active engagement with at least one spring element configured as a spring washer, and of at least one notching plug positioned on the other component for insertion of the at least two notching hooks, in order thereby to ensure secure location and water-tight notching connection of the components.

Further characteristics and advantages of the invention can be seen from the appended illustrations, in which two embodiments of an inventive medical-engineering coupling mechanism are presented only in schematic form, without restricting the invention to these embodiments.

BRIEF DESCRIPTION OF THE DRAWINGS

FIG. 5a shows a cut-out side view of the coupling mechanism of FIG. 1 with the covering cap in place before notching connection of the coupling socket and coupling plug.

FIG. 5b shows a non-cut-out aerial view of the coupling socket according to FIG. 5a but without the covering cap and without the coupling plug.

FIG. 6a shows a view according to FIG. 5a but depicting the coupling mechanism during the insertion of the coupling plug.

FIG. 6b shows a non-cut-out aerial view of the coupling socket according to FIG. 6a but without the covering cap and without the coupling plug.

FIG. 7a shows a view according to FIG. 5a but depicting the coupling mechanism with the coupling socket and coupling plug connected.

FIG. 7b shows a non-cut-out aerial view of the coupling socket according to FIG. 7a but without the covering cap and without the coupling plug.

FIG. 8 shows an enlarged view of FIG. 7a.

FIG. 9 shows a perspective view of a second embodiment of an inventive medical-engineering coupling mechanism consisting of a coupling socket and coupling plug, but without a covering cap for the coupling socket.

FIG. 10 shows a perspective view of the coupling socket according to FIG. 9 without a coupling plug.

FIG. 13a shows a cut-out side view of the coupling mechanism according to FIG. 8 before notching connection of the coupling socket and the coupling plug.

FIG. 13b shows a non-cut-out aerial view of the coupling socket according to FIG. 13a but without the coupling plug.

FIG. 14a shows a view according to FIG. 13a but depicting the coupling mechanism during insertion of the coupling plug.

FIG. 14b shows a non-cut-out aerial view of the coupling socket according to FIG. 14a but without the coupling plug.

FIG. 15a shows a view of FIG. 13a but depicting the coupling mechanism with the coupling socket and coupling plug in notched connection.

FIG. 15b shows a non-cut-out aerial view of the coupling socket according to FIG. 15a but without the coupling plug.

DETAILED DESCRIPTION OF THE INVENTION

Figure 1:
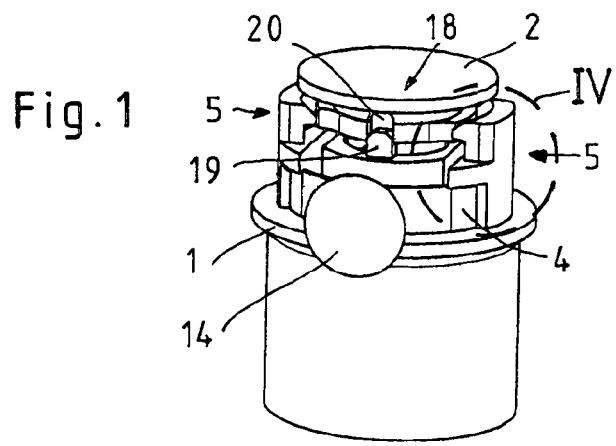
FIG. 1 shows a perspective view of a first embodiment of an inventive medical-engineering coupling mechanism consisting of a coupling socket and coupling plug, but without a covering cap for the coupling socket.

The medical-engineering coupling mechanisms depicted in FIGS. 1 through 15b consist essentially of a coupling socket 1 and a coupling plug 2 that can be secured by notching in the coupling socket 1 by means of a notching connection 3, where the notching connection 3 consists of at least two notching hooks 5 that are in active engagement with at least one spring element 4 configured as a spring washer, and at least one notching recess 6 for inserting the at least two notching hooks 5.

In the illustrated embodiments the notching connection 3 in each case is configured so that the notching hooks 5 are positioned on the coupling sockets 1 and the notching recesses 6 are positioned on the coupling plugs 2. It is also possible of course to configure the notching connection 3 in such a way that the notching hooks 5 are positioned on the coupling plugs 2 and the notching recesses 6 are positioned on the coupling sockets 1. Coupling mechanisms of this type are used to connect two medical instruments, such as an endoscopic instrument and an endoscope lens system, in a water-tight connection to one another.

Figure 2:
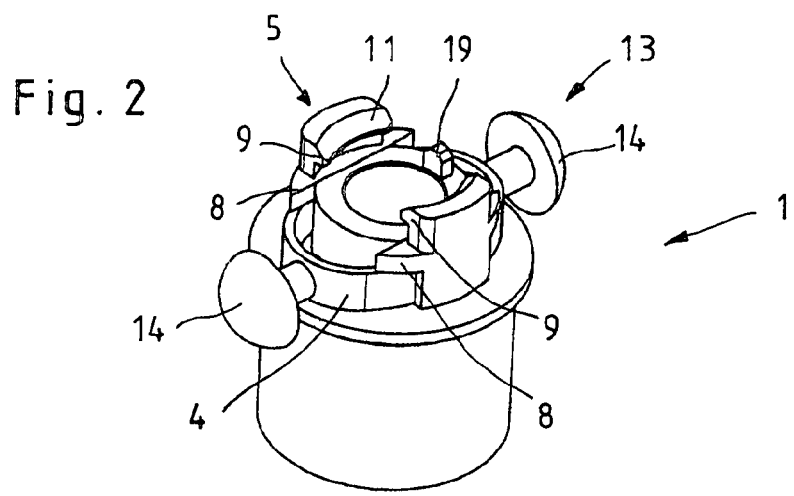
FIG. 2 shows a perspective view of the coupling socket from FIG. 1 without the coupling plug.
Figure 4:
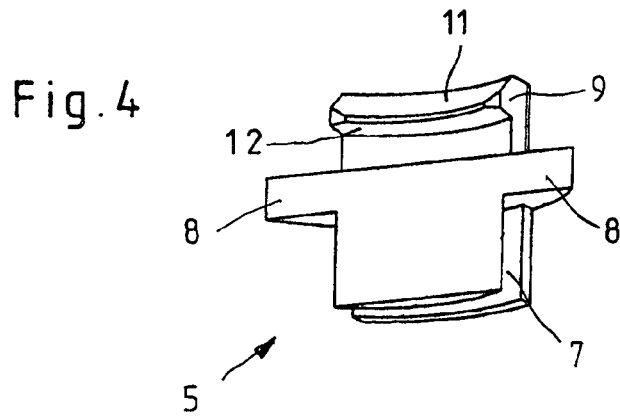
FIG. 4 shows an enlarged perspective view of detail IV from FIG. 1.
Figure 12:
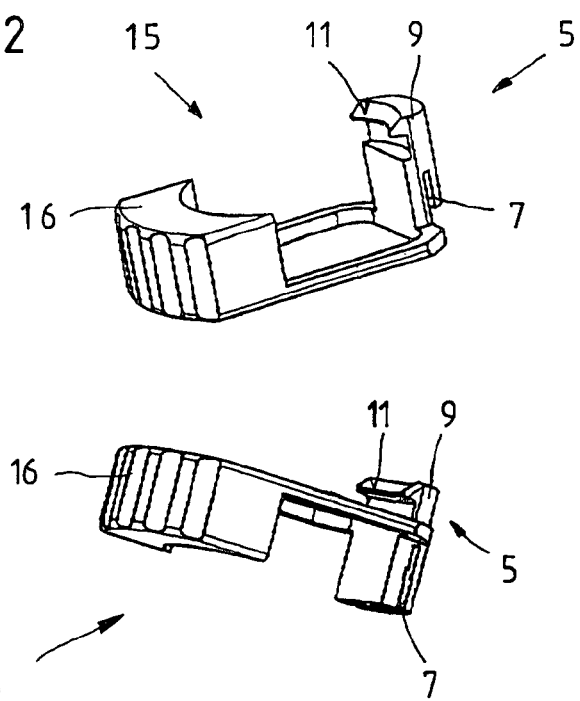
FIG. 12 shows an enlarged perspective view of the sliding member according to FIG. 10.

As can be seen from FIG. 4 seen in relation to FIGS. 1 and 2, and from FIG. 12 seen in relation to FIGS. 9 and 10, the notching hooks 5 are mounted on the spring washer 4, and for this purpose a groove 7 for reception of the spring washer 4 is configured in the housing of the notching hooks 5. To position the spring washer 4, which is mounted in the groove 7, immovably and to prevent any slippage upward, in the embodiment of the notching hooks 5 depicted in FIG. 4 a stud 8 pointing outward is configured on both sides of each of the notching hooks 5 above the groove 7, and the stud 8 is mounted on the spring element 4 when the spring 4 is positioned in the groove 7. In addition the studs 8 serve to position the notching hooks 5 in the notching recess 1.

The actual notching of the notching connection 3 occurs by means of notches 9 which are configured, pointing inward, on the notching hooks 5 and which engage, when connected, in the notching recess 6 configured as a groove 10. In the illustrated embodiment the groove 10 is configured as a surrounding groove 10. To configure the immovable notching, it is of course sufficient to configure grooves 10 for insertion of the respective notches 9 only in certain segments.

To facilitate insertion of the coupling plug 2 in the coupling socket 1 and to simplify notching connection of the notches 9 in the groove 10, starter slopes 11 pointing inward are configured on the upper side of the notches 9 and these starter slopes 11 preferably are at an angle of 45 degrees, so that the notching hooks 5 are automatically pressed outward when they run up against the component that is to be connected by notching.

Figure 8:
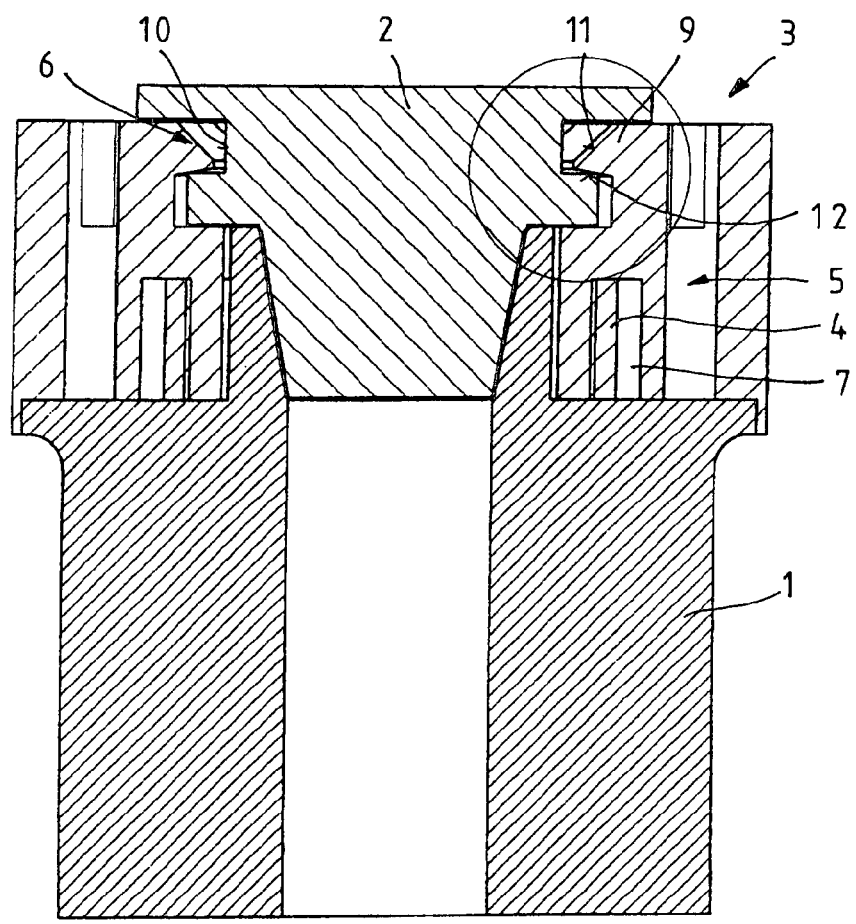

As can be seen in particular from the enlarged view of FIG. 8, bevels 12 pointing inward are configured on the upper side of the notches 9 in order, first, to create a tolerance compensation in configuring the notching hooks 5 and the notching recesses 6 and, second, to ensure a constantly secure, water-tight notching connection. These bevels 12, which advantageously form an angle of 5 to 15 degrees, preferably 10 degrees, to the horizontal plane, interacting with the spring force of the spring washer 4, ensure that the notching connection is always pressed together in the direction of the notching position.

To sever the components 5 and 6 that are connected to one another by the coupling mechanism, the notching connection 3 can be dissolved again by a release mechanism 13 that is in active engagement with the at least one spring element 4.

The first embodiment of the coupling mechanism, illustrated in FIGS. 1 through 8, and the second embodiment, illustrated in FIGS. 9 through 15b, are differentiated from one another with respect to the configuration of the release mechanism 13.

As can be seen in particular from FIGS. 2 and FIGS. 5 through 7b, the release mechanism 13 in the first embodiment consists of two actuation buttons 14 which are positioned on the spring element 4 so that they are offset from the notching hooks 5 and which serve to press the spring element 4 together.

In the illustrated configuration having an elliptical spring washer 4, the notching hooks 5 and the actuation buttons 14 of the release mechanism 13 are alternatingly set off by 90 degrees to one another on the spring washer 4 in such a way that the notching hooks 5 are positioned opposite one another on the longitudinal sides of the spring washer 4 that lie closer to one another, whereas the actuation buttons 14 are positioned opposite one another on the longitudinal sides of the spring washer 4 that lie farther away from one another.

As can be seen in particular from FIG. 10 and FIGS. 13a through 15b, the release mechanism 13 in the second embodiment consists of at least two sliding members 15 so that each sliding member 15 is configured as a single unit with a notching hook 5 in such a way that one actuation part 16 of the sliding member 15 is positioned on the sliding member 15 offset from the respective notching hook 5 by an 180 degree angle. As can be seen from FIGS. 13a through 15b, the spring element 4 can be pressed apart by the sliding member 15 to dissolve the notching connection.

Figure 3:
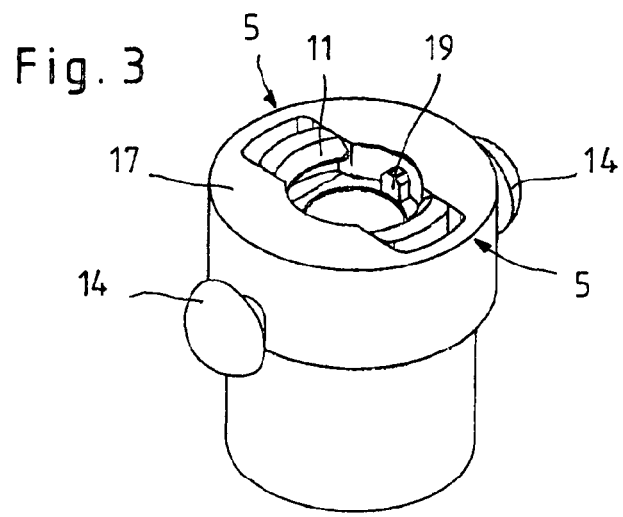
FIG. 3 shows a perspective view according to FIG. 2 but with a covering cap for the coupling socket.
Figure 11:
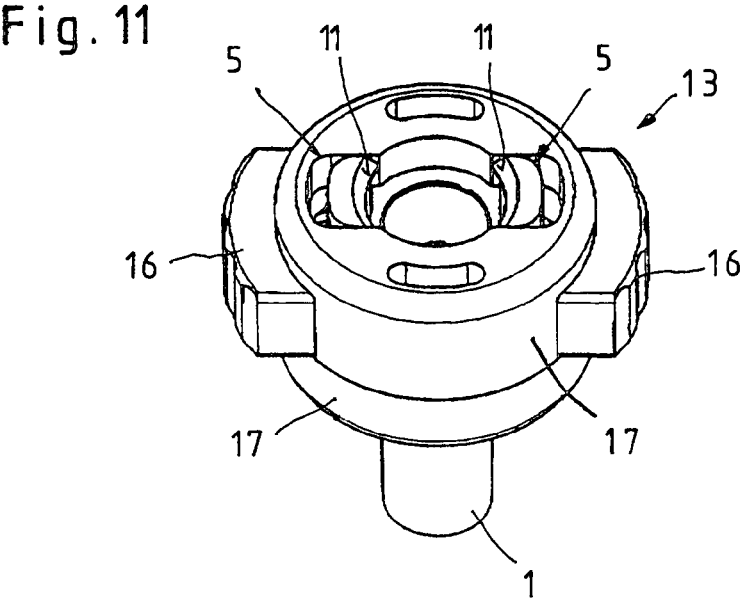
FIG. 11 shows a perspective view according to FIG. 10 but with a covering cap for the coupling socket.

As can further be seen from FIGS. 3 and 11, the coupling sockets 1 can be closed by means of covering caps 17 in such a way that only the insertion area for the coupling plug 2 and the free play for the notching hooks 5 remain uncovered. While the covering cap 17 of the first embodiment, illustrated in FIG. 2, is of one-part structure and is soldered or cemented, for instance, with the coupling socket 1, the covering cap 17 of the second embodiment, illustrated in FIG. 11, is of two-part structure. The two parts of this covering cap can be bolted together, for instance, to cover the coupling recess 1. Likewise it is also possible of course to configure the covering cap 17 of the first embodiment in two parts.

The actuation of the coupling mechanism is explained below with reference to FIGS. 5a through 7b and FIG. 13a through 15b.

To ensure a precisely located and rotation-proof placement of the components coupling socket 1 and coupling plug 2 with respect to one another, there are, as can be seen from FIGS. 1 and 9, guide and/or positioning elements 18 on the coupling plug 2 and on the coupling socket 1 which correspond with one another and which are configured in the illustrated embodiment as centering stud 19 and insertion groove 20.

FIGS. 5a and 13a show the starting position before the reciprocal notching junction of the coupling socket 1 and coupling plug 2. In this position the coupling plug 1 lies above the starter slopes 11 on the notches 9, so that the starter slopes are configured pointing inward at an angle of about 45 degrees.

Now, as soon as an essentially axially acting pressure force to move the two components 1 and 2 toward one another is exerted on the coupling plug 2 and/or on the coupling socket 1, the starter slopes 11 of the notches 9 of the notching hooks 5 cause the notching hooks 5 to be pressed so far outward that the coupling plug 2 assumes the intermediate position shown in FIGS. 6a and 14a.

Because of the exertion of further pressure the coupling plug 2 is moved into the notched position shown in FIGS. 7a and 15a, in which the notches 9 of the notching hooks 5 engage in the groove 10 of the notching recess 6. As can be seen in particular in FIG. 8, the bevels 2 configured on the underside of the notches 9 in this notched position, together with the spring tension of the spring washer 4, cause the notching connection 3 to be pressed, self-inhibiting and water-tight, firmly into the notched position.

The deformation of the spring washer 4 during the notching process can be clearly recognized in the aerial views of FIGS. 5b through 7b and FIGS. 13b through 15b.

To dissolve the notching connection, in the first embodiment, shown in FIGS. 1 through 8, the spring washer 4 is pressed together by the actuation buttons 14 until the notches 9 of the notching hooks 5 go out of engagement with the groove 10 of the notching recesses 6.

In the second embodiment, shown in FIGS. 9 through 15b, the spring washer 4 is pressed apart by pressure exerted on the actuation parts 16 of the sliding member 15 until the notching hooks 5 configured as a single unit with the sliding members 15 have moved so far outward that the notches 9 go out of engagement with the groove 10.

Medical-engineering coupling mechanisms of this configuration are characterized in that merely by pressing together the components 1 and 2 that are to be connected with one another, they cause a water-tight connection.

What is claimed is:

1. A medical-engineering coupling mechanism for connecting two medical instruments having:
 a coupling plug and a coupling socket for insertion of the coupling plug, so that the coupling socket and the coupling plug can be secured to one another by at least one spring-loaded notching connection,
 with the notching connection comprising at least two notching hooks that are positioned on one of the coupling plug and the coupling socket, where the at least two notching hooks are in active engagement with at least one spring element configured as an elliptical spring washer, and at least one notching recess positioned on the other one of the coupling plug and the coupling socket for insertion of the at least two notching hooks; and
 characterized in that in the coupled position the at least one spring element presses the at least two notching hooks into the at least one notching recess and in that the notching connection is releasable by a release mechanism that is in active engagement with the at least one spring element and wherein the at least one spring element is positioned in a groove configured inside the notching hooks with the notching hooks sitting upright on the spring element and that in the coupled position the spring element fixes the notching hooks into the at least one notching recess and in the release position the at least one spring element presses the notching hooks out of the at least one notching recess.

2. A medical-engineering coupling mechanism according to claim 1, characterized in that the spring washer has an elliptical shape when seen in aerial view.

3. A medical-engineering coupling mechanism according to claim 2, characterized in that the at least one spring element consists of metal.

4. A medical-engineering coupling mechanism according to claim 3, characterized in that the at least one spring element consists of precious metal.

5. A medical-engineering coupling mechanism according to claim 1, characterized in that at least one stud is configured pointing outward on each of the notching hooks in the area above the groove and comes in contact with the spring element when the spring element is positioned in the groove.

6. A medical-engineering coupling mechanism according to claim 1, characterized in that the notching hooks are configured on the coupling socket and the notching recess is configured on the coupling plug.

7. A medical-engineering coupling mechanism according to claim 1, characterized in that notches pointing inward are configured on the notching hooks and, when the notching connection is formed, engage in the at least one notching recess wherein each notching recess being configured as a groove.

8. A medical-engineering coupling mechanism according to claim 7, characterized in that starter slopes pointing inward are configured on the upper side of the notches.

9. A medical-engineering coupling mechanism according to claim 7, characterized in that bevels are configured on the underside of the notches.

10. A medical-engineering coupling mechanism according to claim 9, characterized in that the bevels are at an angle of 5 to 15 degrees to the horizontal plane.

11. A medical-engineering coupling mechanism according to claim 7, characterized in that the groove is circular.

12. A medical-engineering coupling mechanism according to claim 1, characterized in that the release mechanism includes at least two actuation buttons positioned opposite to each other on the elliptical spring washer via which regions of the elliptical spring washer on which the actuation buttons are positioned can be pressed towards each other.

13. A medical-engineering coupling mechanism according to claim 1, characterized in that the release mechanism includes at least two sliding members, so that each sliding member is configured as a single unit with a notching hook in such a way that an actuation part of the sliding member is positioned on the sliding member at a displacement of 180 degrees from the respective notching hook.

14. A medical-engineering coupling mechanism according to claim 1, characterized in that guide or positioning elements that correspond with one another are configured on the coupling plug and on the coupling socket.

* * * * *